United States Patent [19]

Colby

[11] 4,249,060
[45] Feb. 3, 1981

[54] METHOD FOR INTRAORALLY WELDING DENTAL APPLIANCES

[76] Inventor: Leigh Colby, 2638 W. River Pkwy., Minneapolis, Minn. 55406

[21] Appl. No.: 1,537

[22] Filed: Jan. 8, 1979

[51] Int. Cl.³ .............................................. B23K 27/00
[52] U.S. Cl. ................................. 219/121 LD; 433/24
[58] Field of Search .... 219/121 L, 121 LM, 121 LD, 219/121 LC; 128/92 R; 3/1.9; 32/14 A, 14 C; 433/24

[56] References Cited

U.S. PATENT DOCUMENTS

| | | | |
|---|---|---|---|
| 3,597,579 | 8/1971 | Lumley | 219/121 LM |
| 3,745,653 | 7/1973 | Cohl | 32/14 A |
| 3,924,332 | 12/1975 | Rauch et al. | 32/14 A |
| 3,949,477 | 4/1976 | Cohen et al. | 32/14 A |
| 4,032,743 | 6/1977 | Erbach et al. | 219/121 LM |
| 4,063,360 | 12/1977 | Waller | 32/14 A |
| 4,150,278 | 4/1979 | Resener | 219/121 LM |

*Primary Examiner*—C. L. Albritton
*Attorney, Agent, or Firm*—Merchant, Gould, Smith, Edell, Welter & Schmidt

[57] ABSTRACT

This invention relates to a method for intraoral microwelding of dental appliances without destruction of oral tissues. The process is practiced by employing a high power laser with power limited to 12 joules per pulse for 8 milliseconds at a wavelength of 1.06 microns. The method contemplates employing a lens with such laser as would yield a spot weld of 0.010 to 0.030 inch diameter.

3 Claims, No Drawings

METHOD FOR INTRAORALLY WELDING DENTAL APPLIANCES

The use of orthodonic appliances and periodontic splints is widespread. However, present art dictates that a weldment of an orthodontic appliance be accomplished externally from the patient's mouth. This necessitates time consuming adjustment after installation of a prewelded appliance. One problem in employing welding of appliances intraorally is that of the heat involved. The heat can injure the patient or break down or destroy tooth tissue.

Similar problems occur in the installation of periodontic splints or archwires. In present usage such archwires are tied into position with ligature wires, a time consuming and exacting procedure to accomplish accurate results.

The present invention is a method for employing a laser to accomplish intraoral welds of such appliances without damage or injury to the patient's tooth or oral tissues. It is best practiced and most advantageous for one time applications in which a high degree of retention is desired, (i.e., periodontal or ortho-surgical splints), or for long term oral devices (archwires, auxiliaries, retainers and so forth) which must withstand the forces of prolonged use without adjustment.

In the present method, a high power industrial neodymium laser capable of delivering 20 joules per pulse for a maximum of 8 milliseconds at a wavelength of 1.06 microns is employed. A lens adapted to yield an effective spot weld at the workpiece of 0.010 to 0.030 inch diameter is employed. A 6 millisecond pulse is effective to accomplish the required welds with an energy of 4 to 8 joules per pulse depending upon the depth of weld desired.

It is extremely important to limit the energy and pulse lengths as set forth above. To lengthen or strengthen the pulse would damage tooth tissue. Also the pulse strength should not be below the specified level or an insufficient or weak weld will result. Higher pulse energies and long pulse lengths may be employed on materials which can withstand such levels, but must be used judiciously.

In practice the laser is set to desired power levels within the parameters set forth. The appliances are placed in the desired location and the laser is activated. The result is an accurately placed positioned (custom fit to the patient's mouth) weldment. No solder flux or soldering aids need be employed to accomplish a secure weld.

It is obvious that a similar method may be applicable to welding orthopedic prosthetic devices during surgery without damage to surrounding human tissue.

I claim:

1. A method for intraoral microwelding of intra-oral appliances comprising the steps of:
   (a) locating an appliance at an intraoral area where the appliance is to be welded;
   (b) irradiating a spot on the appliance to weld the spot with high power radiation provided by a laser with energy between approximately 4 and 8 joules per laser pulse and for a duration of approximately 6 milliseconds; and
   (c) focusing said radiation on the spot to an area between approximately 0.010 and 0.015 inches whereby a weld is formed without causing damage to a tooth.

2. A method in accordance with claim 1 wherein the focusing of step (c) is accomplished by disposing a lens between the laser and the appliance.

3. A method in accordance with claim 1 wherein step (b) includes using a neodymium laser as the energy source.

* * * * *